(12) United States Patent
Mizohata et al.

(10) Patent No.: US 11,890,072 B2
(45) Date of Patent: Feb. 6, 2024

(54) ROBOTIC SURGICAL SYSTEM, PATIENT-SIDE APPARATUS, AND CONTROL METHOD OF ROBOTIC SURGICAL SYSTEM

(71) Applicants: KAWASAKI JUKOGYO KABUSHIKI KAISHA, Kobe (JP); MEDICAROID CORPORATION, Kobe (JP)

(72) Inventors: Yuichi Mizohata, Akashi (JP); Nobuyasu Shimomura, Kobe (JP); Ayataka Kobayashi, Kakogawa (JP)

(73) Assignees: KAWASAKI JUKOGYO KABUSHIKI KAISHA, Kobe (JP); MEDICAROID CORPORATION, Kobe (JP)

( * ) Notice: Subject to any disclaimer, the term of this patent is extended or adjusted under 35 U.S.C. 154(b) by 337 days.

(21) Appl. No.: 17/500,150

(22) Filed: Oct. 13, 2021

(65) Prior Publication Data

US 2022/0110702 A1 Apr. 14, 2022

(30) Foreign Application Priority Data

Oct. 14, 2020 (JP) .................. 2020-173392

(51) Int. Cl.
*A61B 34/00* (2016.01)
*A61B 34/37* (2016.01)
*B25J 9/16* (2006.01)

(52) U.S. Cl.
CPC .............. *A61B 34/70* (2016.02); *A61B 34/37* (2016.02); *B25J 9/1602* (2013.01)

(58) Field of Classification Search
CPC ......... A61B 34/70; A61B 34/37; B25J 9/1602
See application file for complete search history.

(56) References Cited

U.S. PATENT DOCUMENTS

| | | | |
|---|---|---|---|
| 6,394,998 B1 | 5/2002 | Wallace et al. | |
| 6,793,652 B1 | 9/2004 | Whitman et al. | |
| 7,597,025 B2* | 10/2009 | Narita | B25J 19/0029 |
| | | | 901/23 |
| 11,026,758 B2* | 6/2021 | Mintz | A61B 90/50 |
| 2005/0204850 A1* | 9/2005 | Nihei | B25J 9/102 |
| | | | 74/490.01 |
| 2015/0032151 A1 | 1/2015 | Ishida et al. | |
| 2015/0045954 A1* | 2/2015 | Negishi | B25J 9/1607 |
| | | | 700/262 |
| 2015/0128749 A1* | 5/2015 | Gilchrist | B25J 9/042 |
| | | | 74/490.04 |

(Continued)

FOREIGN PATENT DOCUMENTS

| | | |
|---|---|---|
| JP | 2013-215505 A | 10/2013 |
| JP | 2014-195673 A | 10/2014 |
| JP | 2018-505739 A | 3/2018 |

*Primary Examiner* — Jeff A Burke
*Assistant Examiner* — Mohamad O El Sayah
(74) *Attorney, Agent, or Firm* — METROLEX IP LAW GROUP, PLLC

(57) ABSTRACT

A robotic surgical system includes a controller configured or programmed to change a length between a first axis and a second axis in a direction in which a shaft extends, the length serving as a control parameter, according to a rotation speed of the shaft with respect to an amount of operation to control operation of a surgical instrument.

20 Claims, 11 Drawing Sheets

(56) References Cited

U.S. PATENT DOCUMENTS

| | | |
|---|---|---|
| 2016/0113672 A1* | 4/2016 | Aranyi ............ A61B 17/320092 |
| | | 606/169 |
| 2018/0014897 A1 | 1/2018 | Peine |
| 2018/0049818 A1* | 2/2018 | Yates ......................... B25J 9/04 |
| 2018/0085919 A1* | 3/2018 | Nagamatsu ............ B25J 9/1633 |
| 2019/0143513 A1* | 5/2019 | Rabindran ............ B25J 9/1641 |
| | | 700/245 |
| 2019/0374299 A1 | 12/2019 | Peine |
| 2020/0290199 A1* | 9/2020 | Imai ......................... B25J 9/123 |
| 2021/0093405 A1* | 4/2021 | Betsugi .................. A61B 34/37 |

\* cited by examiner

TCP2
TCP

ROBOTIC SURGICAL SYSTEM, PATIENT-SIDE APPARATUS, AND CONTROL METHOD OF ROBOTIC SURGICAL SYSTEM

CROSS-REFERENCE TO RELATED APPLICATION

The present application claims priority to JP2020-173392, which is incorporated herein by reference.

BACKGROUND OF THE INVENTION

Field of the Invention

The present disclosure relates to a robotic surgical system, a patient-side apparatus, and a control method of a robotic surgical system, and more particularly, it relates to a robotic surgical system, a patient-side apparatus, and a control method of a robotic surgical system to control movement of a surgical instrument based on the amount of operation received by an operation unit.

Description of the Background Art

Conventionally, a robotic surgical system including an arm, a tool (surgical instrument) connected to the end of the arm, and an input handle (operation unit) is known. For example, a technology that controls movement of a surgical instrument based on the amount of operation received by an operation unit is disclosed in Japanese Translation of PCT International Application Publication No. 2018-505739. In Japanese Translation of PCT International Application Publication No. 2018-505739, a tool moves within the patient's body, which is a surgical site.

Furthermore, for example, U.S. Pat. No. 6,394,998 discloses a surgical instrument including a shaft, a wrist member having a base end rotatably attached to the tip end of the shaft, and an end effector (forceps) rotatably attached to the tip end of the wrist member as a tool described above.

In the configuration in which the surgical instrument is attached to the tip end of the arm, when the shaft is rotated at a relatively high speed while the end effector is rotated so as to be tilted with respect to the shaft, the amount of movement of the tip end side of the end effector per unit time is relatively large. Consequently, the amount of movement of the arm becomes large, and the arm may vibrate.

SUMMARY OF THE INVENTION

The present disclosure is intended to solve the above problem. The present disclosure aims to provide a robotic surgical system, a patient-side apparatus, and a control method of a robotic surgical system each capable of significantly reducing or preventing vibrations of a manipulator arm even when a shaft of a surgical instrument is rotated at high speed.

In order to attain the aforementioned object, a robotic surgical system according to a first aspect of the present disclosure includes a patient-side apparatus including a manipulator arm to which a surgical instrument is attached to a tip end side of the manipulator arm, an operator-side apparatus including an operation unit to receive an operation on the surgical instrument, and a controller configured or programmed to control operation of the surgical instrument based on an amount of operation corresponding to the operation. The surgical instrument includes an end effector, a first support, a second support, and a shaft connected to the second support, the first support supports the end effector such that the end effector is rotatable about a first axis that is orthogonal to a direction in which the shaft extends, the second support supports the first support such that the first support is rotatable about a second axis that is spaced apart from the first axis in the direction in which the shaft extends and is orthogonal to the direction in which the shaft extends and the first axis, and the controller is configured or programmed to change a length between the first axis and the second axis in the direction in which the shaft extends, the length serving as a control parameter, according to a rotation speed of the shaft with respect to the amount of operation to control the operation of the surgical instrument.

A patient-side apparatus according to a second aspect of the present disclosure includes a manipulator arm to which a surgical instrument is attached to a tip end side of the manipulator arm, and a controller configured or programmed to control operation of the surgical instrument based on an amount of operation corresponding to an operation on the surgical instrument received by an operation unit. The surgical instrument includes an end effector, a first support, a second support, and a shaft connected to the second support, the first support supports the end effector such that the end effector is rotatable about a first axis that is orthogonal to a direction in which the shaft extends, the second support supports the first support such that the first support is rotatable about a second axis that is spaced apart from the first axis in the direction in which the shaft extends and is orthogonal to the direction in which the shaft extends and the first axis, and the controller is configured or programmed to change a length between the first axis and the second axis in the direction in which the shaft extends, the length serving as a control parameter, according to a rotation speed of the shaft with respect to the amount of operation to control the operation of the surgical instrument.

A control method according to a third aspect of the present disclosure is executed by a controller of a robotic surgical system, and the robotic surgical system includes a patient-side apparatus including a manipulator arm to which a surgical instrument is attached to a tip end side of the manipulator arm, an operator-side apparatus including an operation unit to receive an operation on the surgical instrument, and the controller. The surgical instrument includes an end effector, a first support, a second support, and a shaft connected to the second support, the first support supports the end effector such that the end effector is rotatable about a first axis that is orthogonal to a direction in which the shaft extends, and the second support supports the first support such that the first support is rotatable about a second axis that is spaced apart from the first axis in the direction in which the shaft extends and is orthogonal to the direction in which the shaft extends and the first axis. The control method includes receiving an amount of operation corresponding to the operation on the surgical instrument received by the operation unit, and changing a length between the first axis and the second axis in the direction in which the shaft extends, the length serving as a control parameter, according to a rotation speed of the shaft with respect to the amount of operation to control operation of the surgical instrument.

The foregoing and other objects, features, aspects and advantages of the present disclosure will become more apparent from the following detailed description of the present disclosure when taken in conjunction with the accompanying drawings.

DESCRIPTION OF THE PREFERRED EMBODIMENTS

Figure 1:
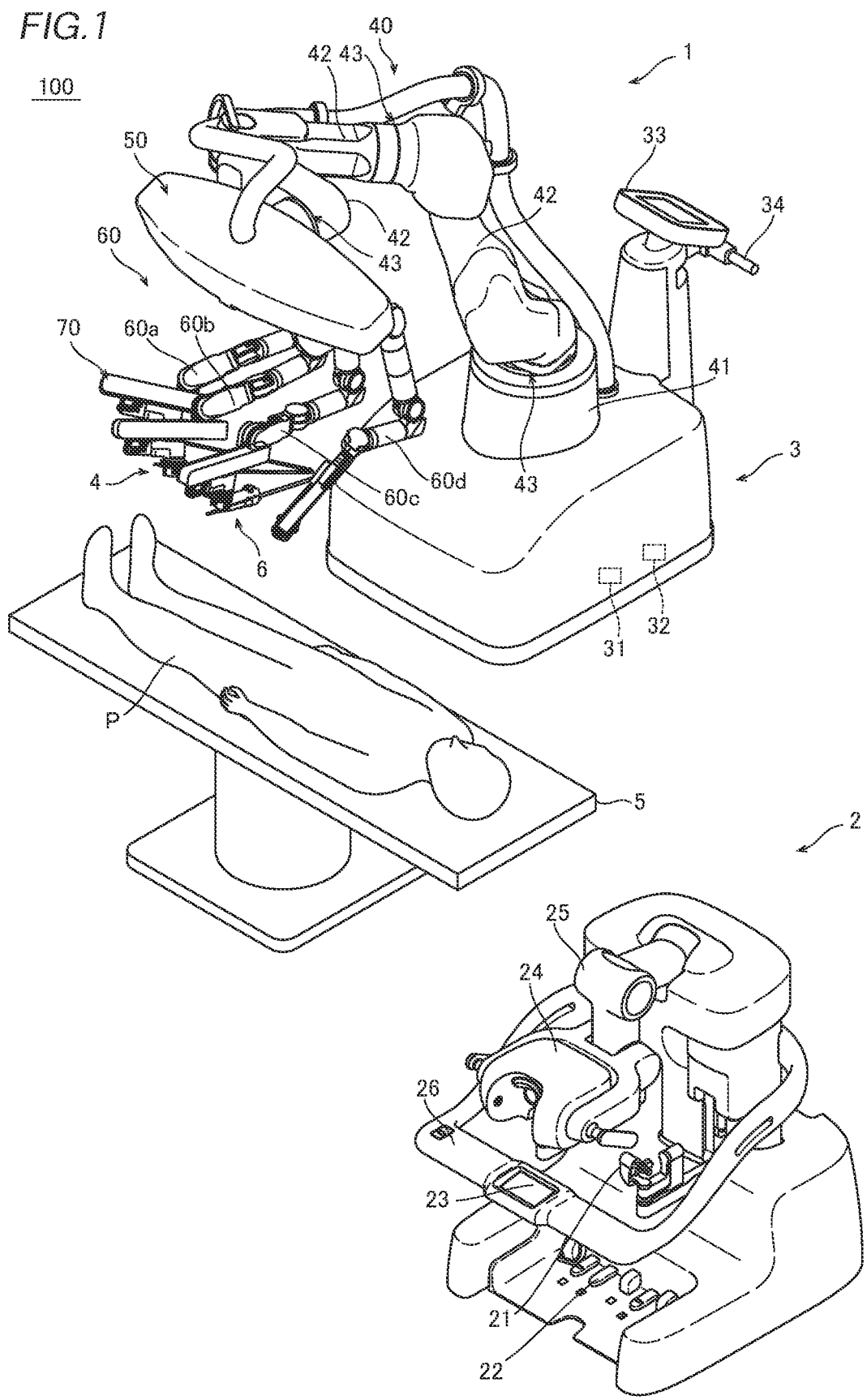
FIG. 1 is a diagram showing the configuration of a surgical system according to an embodiment of the present disclosure.

An embodiment of the present disclosure is hereinafter described with reference to the drawings.

The configuration of a surgical system 100 according to this embodiment is now described with reference to FIGS. 1 to 14. The surgical system 100 includes a medical manipulator 1 that is a patient P-side device and a remote operation device 2 that is an operator-side apparatus to operate the medical manipulator 1. The medical manipulator 1 includes a medical cart 3 and is movable. The remote operation device 2 is spaced apart from the medical manipulator 1, and the medical manipulator 1 is remotely operated by the remote operation device 2. A surgeon inputs a command to the remote operation device 2 to cause the medical manipulator 1 to perform a desired operation. The remote operation device 2 transmits the input command to the medical manipulator 1. The medical manipulator 1 operates based on the received command. The medical manipulator 1 is arranged in an operating room that is a sterilized sterile field. The surgical system 100 is an example of a "robotic surgical system" in the claims.

The remote operation device 2 is arranged inside or outside the operating room, for example. The remote operation device 2 includes operation manipulator arms 21, operation pedals 22, a touch panel 23, a monitor 24, a support arm 25, and a support bar 26. The operation manipulator arms 21 define operation handles for the surgeon to input commands.

The operation manipulator arms 21 receive the amount of operation for the surgical instrument 4. The monitor 24 is a scope-type display that displays an image captured by an endoscope 6. The support arm 25 supports the monitor 24 so as to align the height of the monitor 24 with the height of the surgeon's face. The touch panel 23 is arranged on the support bar 26. The surgeon's head is detected by a sensor (not shown) provided in the vicinity of the monitor 24 such that the medical manipulator 1 can be operated by the remote operation device 2. The surgeon operates the operation manipulator arms 21 and the operation pedals 22 while visually recognizing an affected area on the monitor 24. Thus, a command is input to the remote operation device 2. The command input to the remote operation device 2 is transmitted to the medical manipulator 1. The operation manipulator arms 21 are examples of an "operation unit" in the claims.

The medical cart 3 includes a controller 31 that controls the operation of the medical manipulator 1 and a storage 32 that stores programs or the like to control the operation of the medical manipulator 1. The controller 31 of the medical cart 3 controls the operation of the medical manipulator 1 based on the command input to the remote operation device 2.

The medical cart 3 includes an input 33. The input 33 receives operations to move a positioner 40, an arm base 50, and a plurality of manipulator arms 60 or change their postures mainly in order to prepare for surgery before the surgery.

Figure 2:
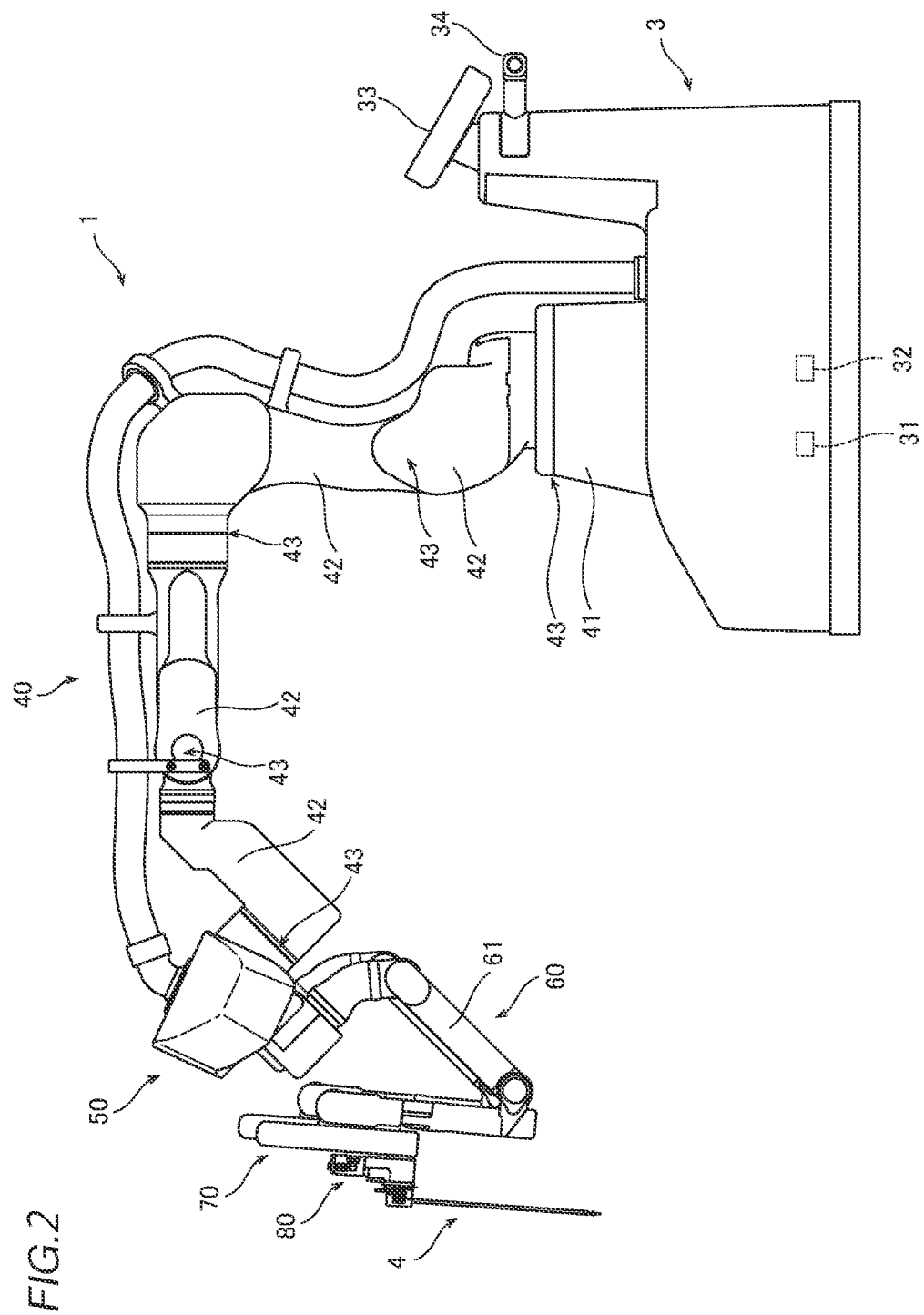
FIG. 2 is a diagram showing the configuration of a medical manipulator according to the embodiment of the present disclosure.

The medical manipulator 1 shown in FIGS. 1 and 2 is arranged in the operating room. The medical manipulator 1 includes the medical cart 3, the positioner 40, the arm base 50, and the plurality of manipulator arms 60. The arm base 50 is attached to the tip end of the positioner 40. The arm base 50 has a relatively long rod shape (long shape). The bases of the plurality of manipulator arms 60 are attached to the arm base 50. Each of the plurality of manipulator arms 60 is able to take a folded posture (stored posture). The arm base 50 and the plurality of manipulator arms 60 are covered with sterile drapes (not shown) and used.

The positioner 40 includes a 7-axis articulated robot, for example. The positioner 40 is arranged on the medical cart 3. The positioner 40 moves the arm base 50. Specifically, the positioner 40 moves the position of the arm base 50 three-dimensionally.

The positioner 40 includes a base 41 and a plurality of links 42 coupled to the base 41. The plurality of links 42 are coupled to each other by joints 43.

As shown in FIG. 1, a surgical instrument 4 is attached to the tip end of each of the plurality of manipulator arms 60. The surgical instrument 4 includes a replaceable instrument or the endoscope 6 (see FIG. 6), for example.

Figure 3:
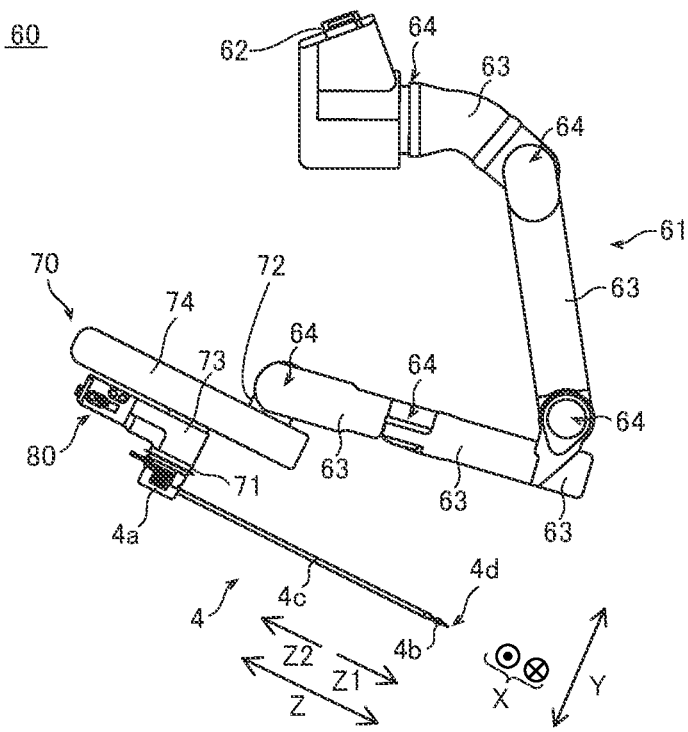
FIG. 3 is a diagram showing the configuration of a manipulator arm according to the embodiment of the present disclosure.

As shown in FIG. 3, the instrument includes a driven unit 4a driven by a servomotor M2 provided in a holder 71 of each of the manipulator arms 60. A pair of forceps 4b is provided as an end effector at the tip end of the instrument. The pair of forceps 4b includes two end effector members 104a and 104b.

Figure 4:
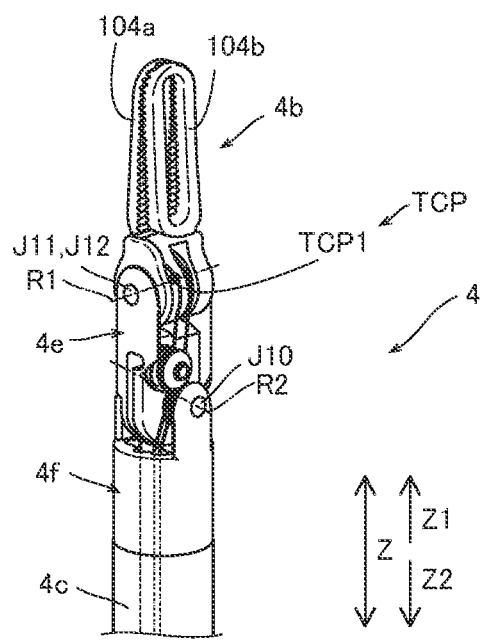
FIG. 4 is a diagram showing a pair of forceps.

As shown in FIG. 4, the instrument includes a first support 4e that supports the base end sides of the end effector members 104a and 104b such that the base end sides of the end effector members 104a and 104b are rotatable about a J11 axis on the tip end sides, a second support 4f that supports the base end side of the first support 4e such that the base end side of the first support 4e is rotatable about a J10 axis on the tip end side, and a shaft 4c connected to the base end side of the second support 4f. The driven unit 4a, the shaft 4c, the second support 4f, the first support 4e, and the pair of forceps 4b are arranged along a Z direction. The J11 axis is orthogonal (z11 direction; see FIG. 12) to a direction (Z direction) in which the shaft 4c extends. The J10 axis is spaced apart from the J11 axis in the direction in which the shaft 4c extends, and is orthogonal (z10 direction; see FIG. 12) to the direction in which the shaft 4c extends and the J11 axis.

The pair of forceps 4b is attached to the first support 4e so as to rotate about the rotation axis R1 of the J11 axis. The second support 4f supports the first support 4e such that the first support 4e is rotatable about the J10 axis. That is, the first support 4e is attached to the second support 4f so as to rotate about the rotation axis R2 of the J10 axis. A portion of the first support 4e on the tip end side (Z1 direction side) has a U-shape. A tool center point (TCP1) is set at the center of the tip end of the U-shaped portion of the first support 4e in a rotation axis R1 direction.

Figure 6:
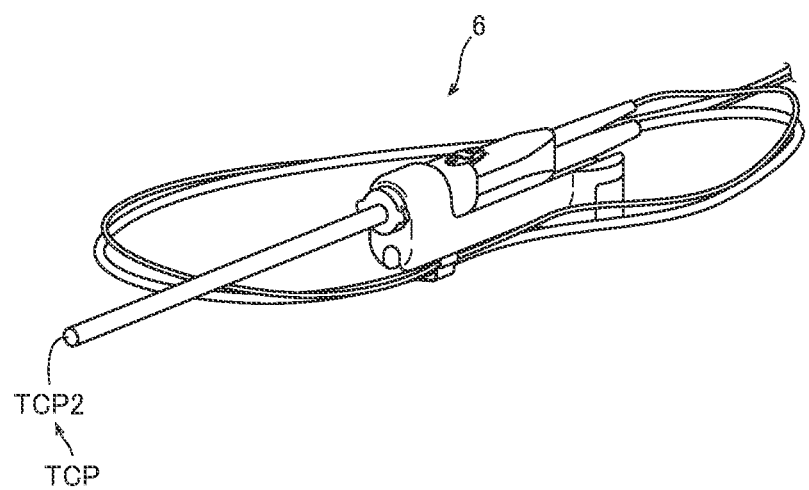
FIG. 6 is a diagram showing an endoscope.
Figure 7:
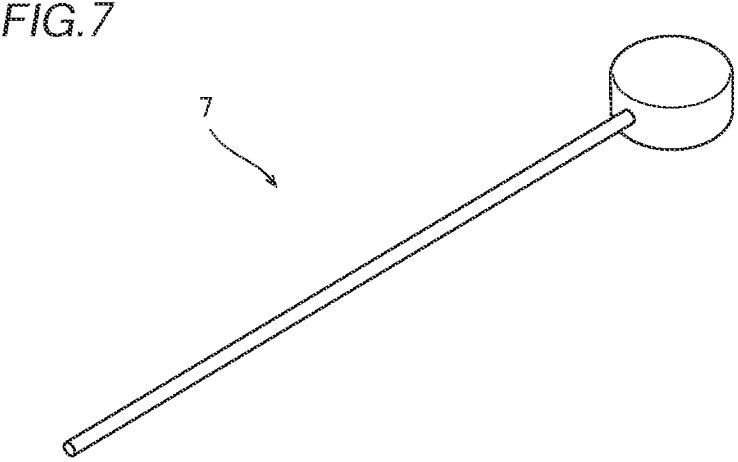
FIG. 7 is a diagram showing a pivot position teaching instrument.

As shown in FIG. 6, a TCP2 of the endoscope 6 is set at the tip end of the endoscope 6.

The configuration of the manipulator arms 60 is now described in detail.

As shown in FIG. 3, each of the manipulator arms 60 includes an arm portion 61 (a base 62, links 63, and joints 64) and a translation mechanism 70 provided at the tip end of the arm portion 61. The tip end sides of the manipulator arms 60 three-dimensionally move with respect to the base sides (arm base 50) of the manipulator arms 60. The plurality of manipulator arms 60 have the same configuration as each other.

The translation mechanism 70 is provided on the tip end side of the arm portion 61, and the surgical instrument 4 is attached thereto. The translation mechanism 70 translates the surgical instrument 4 in a direction in which the surgical instrument 4 is inserted into the patient P. Furthermore, the translation mechanism 70 translates the surgical instrument 4 relative to the arm portion 61. Specifically, the translation mechanism 70 includes the holder 71 that holds the surgical instrument 4. The servomotor M2 (see FIG. 10) is housed in the holder 71. The servomotor M2 rotates a rotating body provided in the driven unit 4a of the surgical instrument 4. The rotating body of the driven unit 4a is rotated such that the pair of forceps 4b is operated.

The arm portion 61 includes a 7-axis articulated robot arm. The arm portion 61 includes the base 62 to attach the arm portion 61 to the arm base 50, and a plurality of links 63 coupled to the base 62. The plurality of links 63 are coupled to each other by the joints 64.

The translation mechanism 70 translates the surgical instrument 4 attached to the holder 71 along the Z direction (the direction in which the shaft 4c extends) by translating the holder 71 along the Z direction. Specifically, the translation mechanism 70 includes a base end side link 72 connected to the tip end of the arm portion 61, a tip end side link 73, and a coupling link 74 provided between the base end side link 72 and the tip end side link 73. The holder 71 is provided on the tip end side link 73.

The coupling link 74 of the translation mechanism 70 is configured as a double speed mechanism that moves the tip end side link 73 relative to the base end side link 72 along the Z direction. The tip end side link 73 is moved along the Z direction relative to the base end side link 72 such that the surgical instrument 4 provided on the holder 71 is translated along the Z direction. The tip end of the arm portion 61 is connected to the base end side link 72 so as to rotate the base end side link 72 about an X direction orthogonal to the Z direction.

Figure 5:
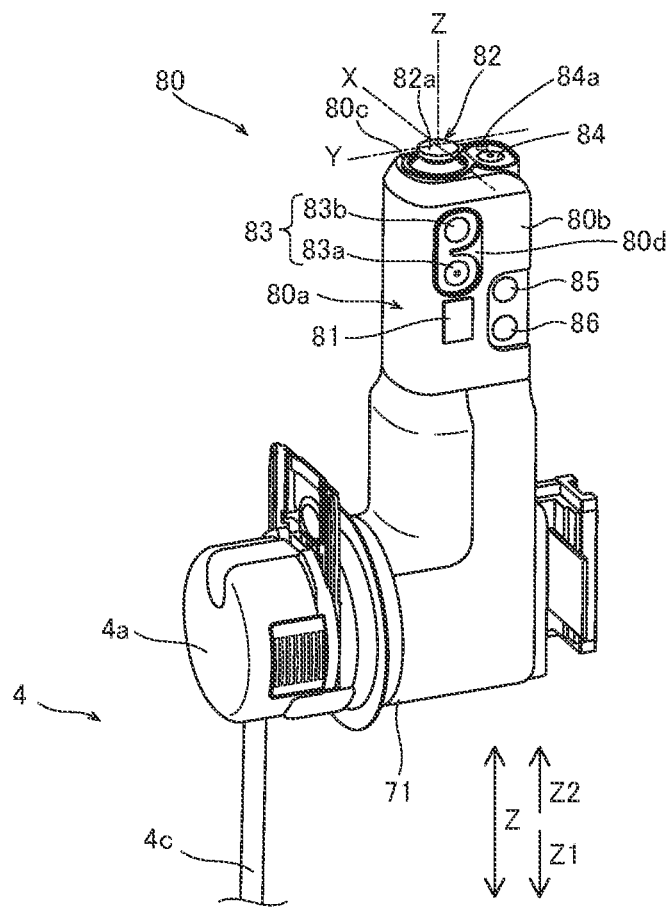
FIG. 5 is a perspective view showing the configuration of an operation unit of the medical manipulator according to the embodiment of the present disclosure.

As shown in FIG. 5, the medical manipulator 1 includes an operation unit 80 attached to each of the manipulator arms 60 to operate the manipulator arm 60. The operation unit 80 includes an enable switch 81, a joystick 82, and a switch unit 83. The enable switch 81 allows or disallows movement of the manipulator arm 60 through the joystick 82 and the switch unit 83. The enable switch 81 gets into a state of allowing movement of the surgical instrument 4 by the manipulator arm 60 when the operator (such as a nurse or an assistant) grasps the operation unit 80 and presses the enable switch 81.

The switch unit 83 includes a switch 83a to move the surgical instrument 4 in the direction in which the surgical instrument 4 is inserted into the patient P, along the longitudinal direction of the surgical instrument 4, and a switch 83b to move the surgical instrument 4 in a direction opposite to the direction in which the surgical instrument 4 is inserted into the patient P. Both the switch 83a and the switch 83b are push-button switches.

As shown in FIG. 5, the operation unit 80 includes a pivot button 85 to teach a pivot position PP that serves as a fulcrum (see FIG. 9) for movement of the surgical instrument 4 attached to the manipulator arm 60. The pivot button 85 is provided adjacent to the enable switch 81 on a surface 80b of the operation unit 80. The pivot button 85 is pressed while the tip end of the endoscope 6 (see FIG. 6) or a pivot position teaching instrument 7 (see FIG. 7) is moved to a position corresponding to the insertion position of a trocar T inserted into the body surface of the patient P such that the pivot position PP is taught and stored in the storage 32. In the teaching of the pivot position PP, the pivot position PP is set as one point (coordinates), and the direction of the surgical instrument 4 is not set.

As shown in FIG. 1, the endoscope 6 is attached to one manipulator arm 60 (manipulator arm 60c, for example) of the plurality of manipulator arms 60, and surgical instruments 4 other than the endoscope 6 are attached to the remaining manipulator arms 60 (manipulator arms 60a, 60b, and 60d, for example). Specifically, in surgery, the endoscope 6 is attached to one of four manipulator arms 60, and the surgical instruments 4 (such as pairs of forceps) other than the endoscope 6 are attached to the three manipulator arms 60. The pivot position PP is taught with the endoscope 6 attached to the manipulator arm 60 to which the endoscope 6 is to be attached. Furthermore, pivot positions PP are taught with pivot position teaching instruments 7 attached to the manipulator arms 60 to which the surgical instruments 4 other than the endoscope 6 are to be attached. The endoscope 6 is attached to one of two manipulator arms 60 (manipulator arms 60b and 60c) arranged in the center among the four manipulator arms 60 arranged adjacent to each other. That is, the pivot position PP is individually set for each of the plurality of manipulator arms 60.

As shown in FIG. 5, an adjustment button 86 for optimizing the position of the manipulator arm 60 is provided on the surface 80b of the operation unit 80. After the pivot position PP for the manipulator arm 60 to which the endoscope 6 has been attached is taught, the adjustment button 86 is pressed such that the positions of the other manipulator arms 60 (arm base 50) are optimized.

Figure 8:
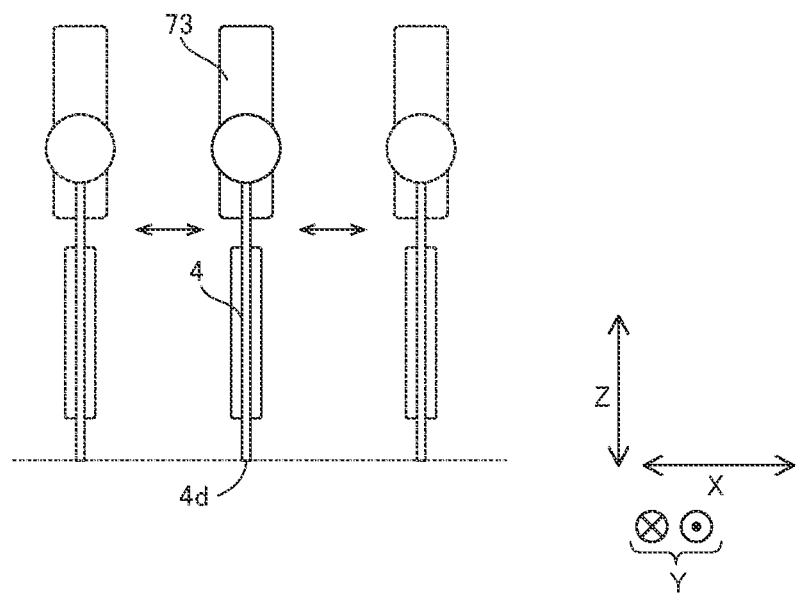
FIG. 8 is a diagram for illustrating translation of the manipulator arm.
Figure 9:
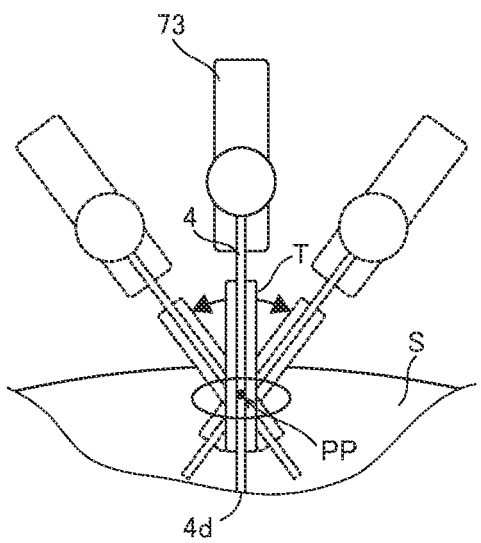
FIG. 9 is a diagram for illustrating rotation of the manipulator arm.

As shown in FIG. 5, the operation unit 80 includes a mode switching button 84 to switch between a mode for translating the surgical instrument 4 attached to the manipulator arm 60 (see FIG. 8) and a mode for rotating the surgical instrument 4 (see FIG. 9). Furthermore, a mode indicator 84a is provided in the vicinity of the mode switching button 84. The mode indicator 84a indicates a switched mode.

Specifically, the mode indicator 84a is turned on (rotation mode) or off (translation mode) such that a current mode (translation mode or rotation mode) is indicated.

The mode indicator 84a also serves as a pivot position indicator that indicates that the pivot position PP has been taught.

As shown in FIG. 8, in the mode for translating the manipulator arm 60, the manipulator arm 60 is moved such that the tip end 4d of the surgical instrument 4 moves on an X-Y plane. As shown in FIG. 9, in the mode for rotating the manipulator arm 60, when the pivot position PP is not taught, the manipulator arm 60 is moved such that the surgical instrument 4 rotates about the pair of forceps 4b, and when the pivot position PP is taught, the manipulator arm 60 is moved such that the surgical instrument 4 rotates about the pivot position PP as a fulcrum. The surgical instrument 4 is rotated while the shaft 4c of the surgical instrument 4 is inserted into the trocar T.

Figure 10:
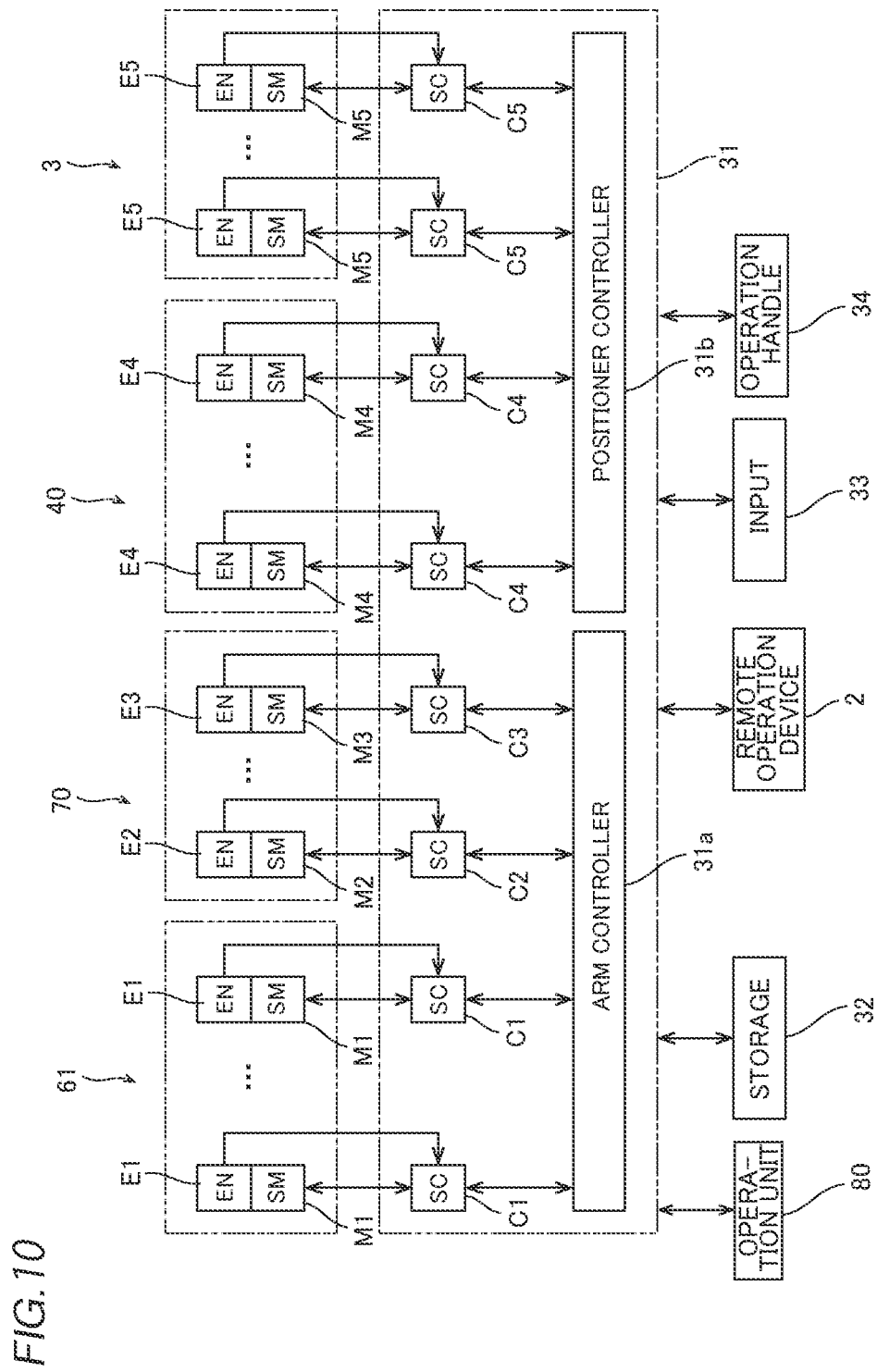
FIG. 10 is a block diagram showing the configuration of a controller of the medical manipulator according to the embodiment of the present disclosure.

As shown in FIG. 10, the manipulator arm 60 includes a plurality of servomotors M1, encoders E1, and speed reducers (not shown) so as to correspond to a plurality of joints 64 of the arm portion 61. The encoders E1 detect the rotation angles of the servomotors M1. The speed reducers slow down rotation of the servomotors M1 to increase the torques.

As shown in FIG. 10, the translation mechanism 70 includes the servomotor M2 to rotate the rotating body provided in the driven unit 4a of the surgical instrument 4, a servomotor M3 to translate the surgical instrument 4, encoders E2 and E3, and speed reducers (not shown). The encoders E2 and E3 detect the rotation angles of the servomotors M2 and M3, respectively. The speed reducers slow down rotation of the servomotors M2 and M3 to increase the torques.

The positioner 40 includes a plurality of servomotors M4, encoders E4, and speed reducers (not shown) so as to correspond to a plurality of joints 43 of the positioner 40. The encoders E4 detect the rotation angles of the servomotors M4. The speed reducers slow down rotation of the servomotors M4 to increase the torques.

The medical cart 3 includes servomotors M5 to drive a plurality of front wheels (not shown) of the medical cart 3, respectively, encoders E5, and speed reducers (not shown). The encoders E5 detect the rotation angles of the servomotors M5. The speed reducers slow down rotation of the servomotors M5 to increase the torques.

The controller 31 of the medical cart 3 includes an arm controller 31a to control movement of the plurality of manipulator arms 60 based on commands, and a positioner controller 31b to control movement of the positioner 40 and driving of the front wheels (not shown) of the medical cart 3 based on commands. Servo controllers C1 that controls the servomotors M1 to drive the manipulator arm 60 are electrically connected to the arm controller 31a. The encoders E1 to detect the rotation angles of the servomotors M1 are electrically connected to the servo controllers C1.

A servo controller C2 that controls the servomotor M2 to drive the surgical instrument 4 is electrically connected to the arm controller 31a. The encoder E2 to detect the rotation angle of the servomotor M2 is electrically connected to the servo controller C2. A servo controller C3 that controls the servomotor M3 to translate the translation mechanism 70 is electrically connected to the arm controller 31a. The encoder E3 to detect the rotation angle of the servomotor M3 is electrically connected to the servo controller C3.

An operation command input to the remote operation device 2 is input to the arm controller 31a. The arm controller 31a generates position commands based on the input operation command and the rotation angles detected by the encoders E1 (E2 or E3), and outputs the position commands to the servo controllers C1 (C2 or C3). The servo controllers C1 (C2 or C3) generate torque commands based on the position commands input from the arm controller 31a and the rotation angles detected by the encoders E1 (E2 or E3), and output the torque commands to the servomotors M1 (M2 or M3). Thus, the manipulator arm 60 is moved according to the operation command input to the remote operation device 2.

The arm controller 31a operates the manipulator arm 60 based on an input signal from the joystick 82 of the operation unit 80. Specifically, the arm controller 31a generates position commands based on the input signal (operation command) input from the joystick 82 and the rotation angles detected by the encoders E1, and outputs the position commands to the servo controllers C1. The servo controllers C1 generate torque commands based on the position commands input from the arm controller 31a and the rotation angles detected by the encoders E1, and output the torque commands to the servomotors M1. Thus, the manipulator arm 60 is moved according to the operation command input to the joystick 82.

The arm controller 31a operates the manipulator arm 60 based on an input signal from the switch unit 83 of the operation unit 80. Specifically, the arm controller 31a generates a position command based on the input signal (operation command) input from the switch unit 83 and the rotation angle detected by the encoders E1 or the encoder E3, and outputs the position command to the servo controllers C1 or the servo controller C3. The servo controllers C1 or the servo controller C3 generates a torque command based on the position command input from the arm controller 31a and the rotation angle detected by the encoders E1 or the encoder E3, and outputs the torque command to the servomotors M1 or the servomotor M3. Thus, the manipulator arm 60 is moved according to the operation command input to the switch unit 83.

As shown in FIG. 10, servo controllers C4 that control the servomotors M4 to move the positioner 40 are electrically connected to the positioner controller 31b. The encoders E4 to detect the rotation angles of the servomotors M4 are electrically connected to the servo controllers C4. Servo controllers C5 that control the servomotors M5 to drive the front wheels (not shown) of the medical cart 3 are electrically connected to the positioner controller 31b. The encoders E5 to detect the rotation angles of the servomotors M5 are electrically connected to the servo controllers C5.

An operation command is input from the input 33 to the positioner controller 31b. The positioner controller 31b generates position commands based on the operation command input from the input 33 and the rotation angles detected by the encoders E4, and outputs the position commands to the servo controllers C4. The servo controllers C4 generate torque commands based on the position commands input from the positioner controller 31b and the rotation angles detected by the encoders E4, and output the torque commands to the servomotors M4. Thus, the positioner 40 is moved according to the operation command input to the input 33. Although detailed description is omitted, the positioner controller 31b moves the medical cart 3 according to an operation command from an operation handle 34 by a similar procedure.

Axes of Manipulator Arm

Axes of the manipulator arm 60 are now described with reference to FIG. 11.

Figure 11:
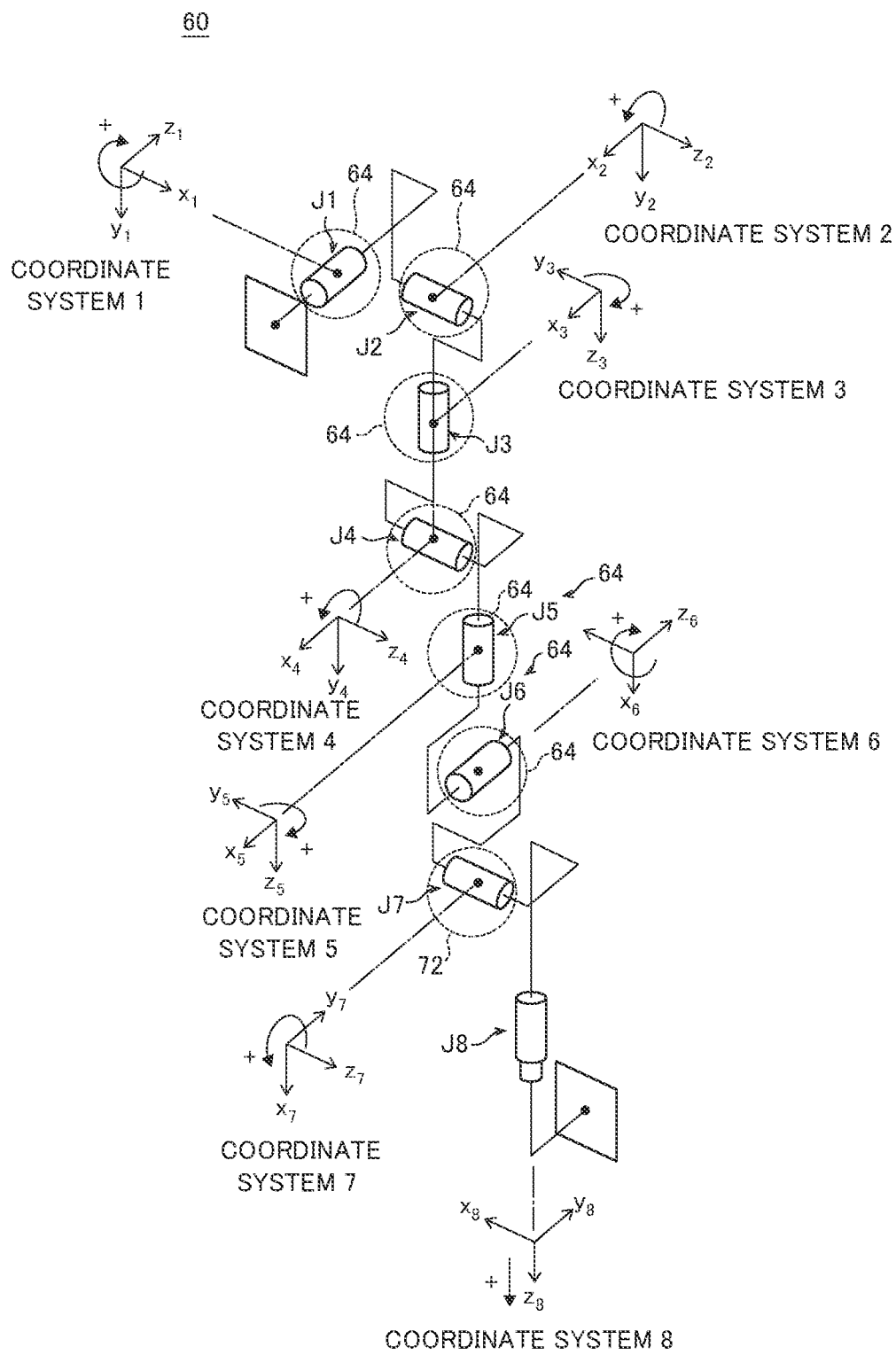
FIG. 11 is a diagram showing rotation axes (linear motion axes) of the manipulator arm.

As shown in FIG. 11, the manipulator arm 60 includes J1 to J7 axes as rotation axes and a J8 axis as a linear motion axis. The J1 to J7 axes correspond to the rotation axes of the joints 64 of the arm portion 61. Furthermore, the J7 axis corresponds to the base end side link 72 of the translation mechanism 70 (see FIG. 3). The J8 axis corresponds to an axis that moves the tip end side link 73 of the translation mechanism 70 relative to the base end side link 72 along the Z direction. That is, the servomotors M1 shown in FIG. 10 are provided so as to correspond to the J1 to J7 axes of the manipulator arm 60. Furthermore, the servomotor M3 is provided so as to correspond to the J8 axis. Coordinate systems 1 to 8 represent the coordinate systems of the J1 to J8 axes, respectively.

Axes of Surgical Instrument (Forceps)

Axes of the surgical instrument 4 (forceps 4b) are now described with reference to FIG. 12.

Figure 12:
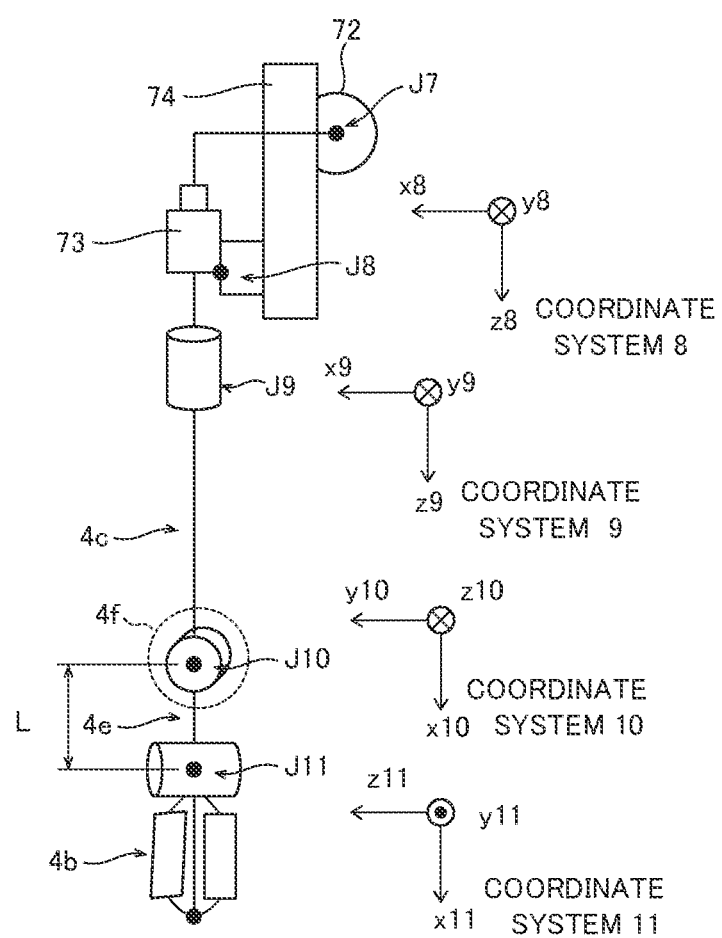
FIG. 12 is a diagram showing rotation axes (linear motion axes) of a translation mechanism and a surgical instrument.

As shown in FIG. 12, the surgical instrument 4 (forceps 4b) includes a J9 axis as a rotation axis (axis along the direction in which the shaft 4c extends) of the shaft 4c, the J10 axis as a rotation axis of the second support 4f connected to the shaft 4c, the J11 axis as an axis about which the pair of forceps 4b rotates with respect to the first support 4e, and a J12 axis as an opening/closing axis of the pair of forceps 4b. A plurality of (four, for example) servomotors M2 provided in the holder 71 of the manipulator arm 60 are provided, and the driven unit 4a is driven by the plurality of servomotors M2. Thus, the surgical instrument 4 is driven around the J9 axis to the J12 axis. The J10 axis and the J11 axis are examples of a "second axis" and a "first axis" in the claims, respectively. The coordinate systems 8 to 11 represent the coordinate systems of the J8 axis to the J11 axis, respectively.

The controller 31 calculates an axis value (command value) to create a target posture for the manipulator arm 60 and the surgical instrument 4 (forceps 4b or endoscope 6) attached to the manipulator arm 60 based on the amount of operation received by the operation manipulator arms 21 of the remote operation device 2. Specifically, the manipulator arm 60 and the pair of forceps 4b (or the endoscope 6) operate around the pivot position PP in response to an operation from the operation manipulator arms 21. A control parameter of the manipulator arm 60, the pivot position PP, and a control parameter of the surgical instrument 4 are used to calculate the command value. The control parameter of the manipulator arm 60 includes a link length (length between the axes). The control parameter of the surgical instrument 4 also includes a link length (length between the axes).

Figure 13:
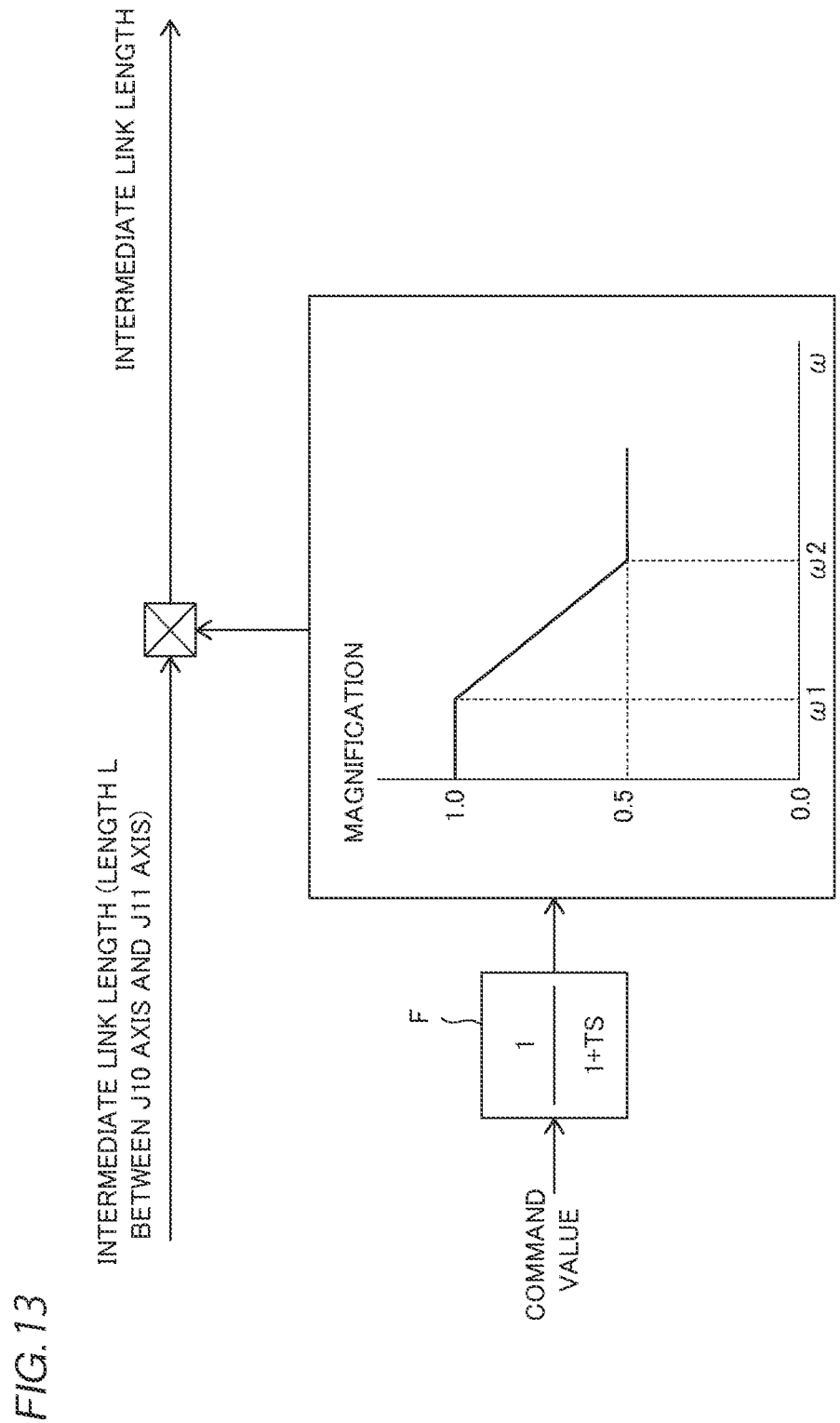
FIG. 13 is a diagram for illustrating a length (control parameter) between a J10 axis and a J11 axis with respect to the rotation speed of a shaft.
Figure 14:
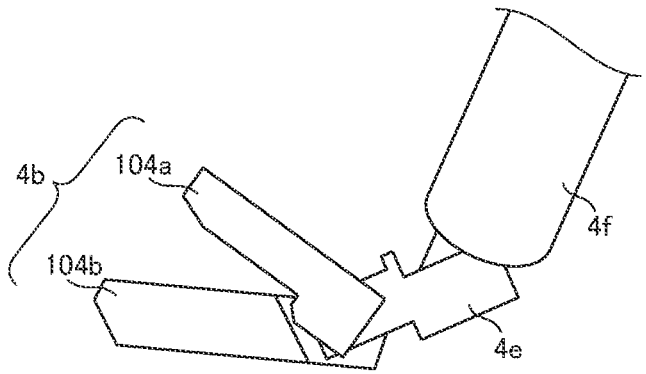
FIG. 14 is a diagram showing the surgical instrument in a state in which the tip end side thereof is bent.

In this embodiment, as shown in FIG. 13, the controller 31 controls the operation of the surgical instrument 4 by changing a length L (see FIG. 12) between the J10 axis and the J11 axis in the direction in which the shaft 4c extends as the control parameter according to the rotation speed ω of the shaft 4c with respect to the amount of operation according to an operation including an action to rotate the surgical instrument 4, received by the operation manipulator arms 21. Specifically, when the rotation speed ω of the shaft 4c (the rotation speed ω of the J9 axis) is equal to or higher than a first rotation speed ω1, the controller 31 controls movement of the surgical instrument 4 by decreasing the length L (intermediate link length) (control parameter) between the J10 axis and the J11 axis. The rotation speed ω of the shaft 4c refers to the rotation speed ω during the shaft 4c rotates about the J9 axis, which is the rotation axis of the shaft 4c, using the pivot position PP as a center. The first rotation speed ω1 is an example of a "predetermined rotation speed" in the claims.

In this embodiment, the controller 31 gradually decreases the length L (control parameter) between the J10 axis and the J11 axis as the rotation speed ω increases. Specifically, the controller 31 linearly decreases the length L (control parameter) between the J10 axis and the J11 axis as the rotation speed ω increases.

Specifically, in this embodiment, when the rotation speed ω is equal to or higher than the first rotation speed ω1 and equal to or lower than a second rotation speed ω2 that is higher than the first rotation speed ω1, the controller 31 decreases the control parameter as the rotation speed ω increases. When the rotation speed ω exceeds the second rotation speed ω2, the controller 31 sets the control parameter to a constant control parameter corresponding to the second rotation speed ω2. For example, assuming that an actual length between the J10 axis and the J11 axis is L, the magnitude of the control parameter corresponding to the second rotation speed ω2 is 0.5 L.

That is, when the rotation speed ω is equal to or higher than the first rotation speed ω1 and equal to or lower than the second rotation speed ω2, the controller 31 calculates the length L between the J10 axis and the J11 axis corresponding to the rotation speed ω by linear interpolation. Furthermore, the controller 31 calculates the length L between the J10 axis and the J11 axis corresponding to the rotation speed ω by multiplying the actual length L between the J10 axis and the J11 axis by the magnification (0.5 or more and 1 or less) corresponding to the rotation speed ω.

In this embodiment, when the rotation speed ω is lower than the first rotation speed ω1, the controller 31 maintains the actual length L between the J10 axis and the J11 axis constant (i.e., multiplies it by the magnification of 1.0) without decreasing it.

For example, the first rotation speed ω1 is a value of 60% of the maximum rotation speed ω of the shaft 4c. For example, the second rotation speed ω2 is a value of 90% of the maximum rotation speed ω of the shaft 4c.

In this embodiment, the controller 31 generates a command value of the rotation speed ω according to the rotation speed ω with respect to the received amount of operation. Then, the controller 31 applies a low-pass filter F to the generated command value. Then, when the command value of the rotation speed ω of the shaft 4c is equal to or higher than the first rotation speed ω1 after the low-pass filter F is applied thereto, the controller 31 decreases the length L between the J10 axis and the J11 axis to control movement of the surgical instrument 4.

The controller 31 constantly operates to change the control parameter based on the rotation speed ω of the shaft 4c during the operation of the medical manipulator 1. That is, the controller 31 operates to change the control parameter based on the rotation speed ω regardless of whether the surgical instrument 4 is bent such that the first support 4e rotates about the J10 axis and intersects with the direction in which the shaft 4c extends (see FIG. 14), or the first support 4e does not rotate about the J10 axis and the surgical instrument 4 is not bent (see FIG. 4). When the shaft 4c is rotated at a relatively high speed while the surgical instrument 4 is bent, vibrations of the manipulator arm 60 appear particularly remarkably. Therefore, decreasing the length L, which is the control parameter, while the surgical instrument 4 is bent is particularly effective in significantly reducing or preventing the vibrations of the manipulator arm 60.

Control Method of Surgical System

Figure 15:
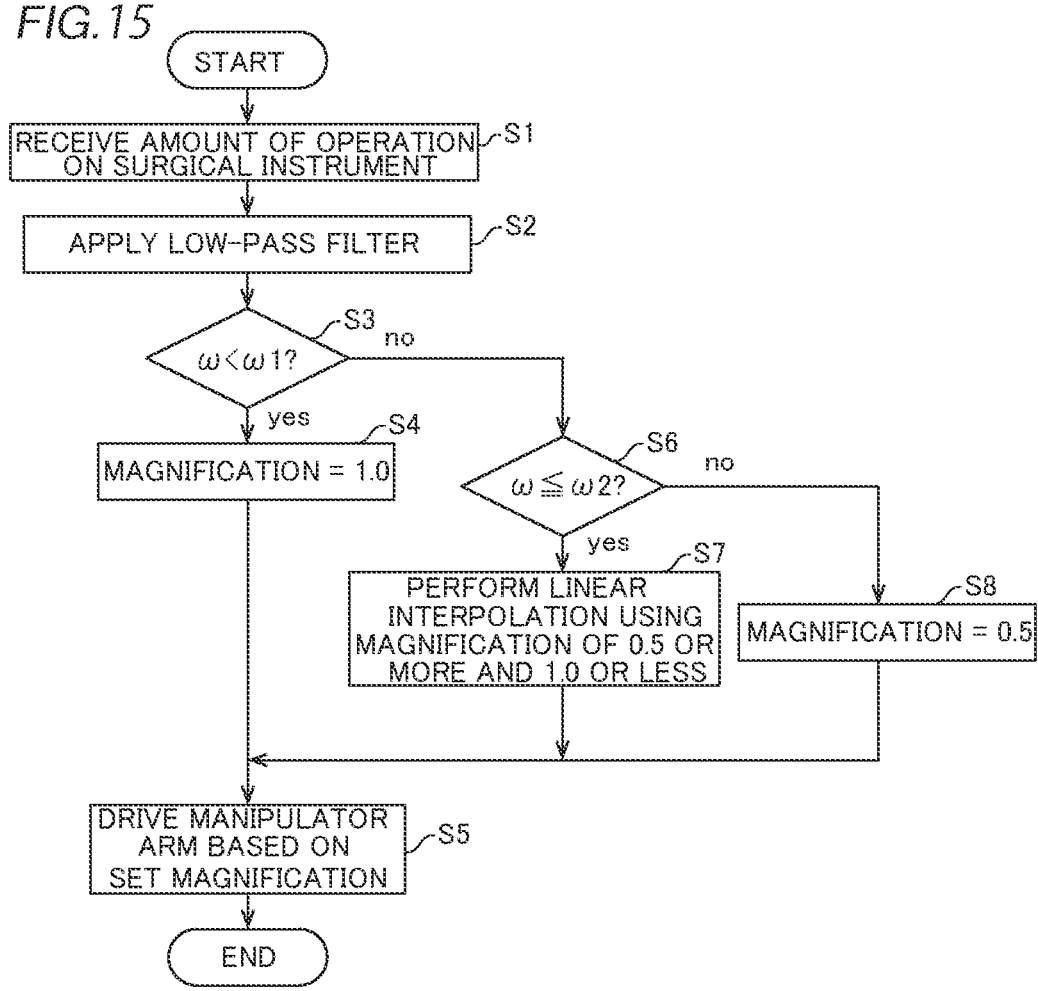
FIG. 15 is a flowchart for illustrating a control method of the surgical system according to the embodiment of the present disclosure.

A control method of the surgical system 100 is now described with reference to FIG. 15.

First, in step S1, the controller 31 receives an operation on the surgical instrument 4, including the action to rotate the surgical instrument 4.

Then, in step S2, the controller 31 applies the low-pass filter F to the rotation speed ω of the shaft 4c according to the received operation.

Then, in step S3, the controller 31 determines whether or not the rotation speed ω of the shaft 4c is lower than the first rotation speed ω1 after the low-pass filter F is applied to the rotation speed ω of the shaft 4c. In the case of yes in step S3, in step S4, the controller 31 sets the magnification by which the length L between the J10 axis and the J11 axis is multiplied to 1.0.

Then, in step S5, the manipulator arm 60 is driven based on the set magnification.

In the case of no in step S3, in step S6, the controller 31 determines whether or not the rotation speed ω of the shaft 4c is equal to or lower than the second rotation speed ω2 after the low-pass filter F is applied to the rotation speed ω of the shaft 4c. In the case of yes in step S6, in step S7, the controller 31 calculates, by linear interpolation, the magnification (0.5 or more and 1.0 or less) by which the actual length L is multiplied, corresponding to the rotation speed ω of the shaft 4c, and changes the length L according to the calculated magnification. Then, the controller 31 advances to step S5.

In the case of no in step S6, in step S8, the controller 31 sets the magnification by which the actual length L is multiplied to 0.5. Then, the controller 31 advances to step S5.

The operations in step S1 to step S8 described above are constantly performed during the operation of the manipulator arm 60, and are performed for each of the plurality of manipulator arms 60.

Advantages of This Embodiment

According to this embodiment, the following advantages are achieved.

Advantages of Surgical System and Medical Manipulator

According to this embodiment, as described above, the controller 31 is configured or programmed to change the length L (control parameter) between the J10 axis and the J11 axis in the direction in which the shaft 4c extends according to the rotation speed ω of the shaft 4c with respect to the amount of operation to control the operation of the surgical instrument 4. Accordingly, when the rotation speed ω of the shaft 4c increases, the length L between the J10 axis and the J11 axis is decreased such that the length L between the tip end (J10 axis) of the shaft 4c and the pair of forceps 4b (J11 axis) is decreased in terms of control. Therefore, when the shaft 4c is rotated at high speed, the amount of movement of the pair of forceps 4b on the tip end side per unit time is decreased such that an increase in the amount of movement of the manipulator arm 60 is significantly reduced or prevented. Consequently, vibrations of the manipulator arm 60 can be significantly reduced or prevented even when the shaft 4c of the surgical instrument 4 is rotated at high speed.

According to this embodiment, as described above, the controller 31 is configured or programmed to gradually decrease the control parameter as the rotation speed ω increases. When the control parameter changes rapidly, the tool center point serving as a control point changes rapidly, and control of the manipulator arm 60 becomes complex. Therefore, the control parameter is gradually decreased as described above such that complex control of the manipulator arm 60 can be significantly reduced or prevented even when the control parameter changes. Furthermore, vibrations of the manipulator arm 60 caused by a rapid change in the tool center point serving as a control point can be significantly reduced or prevented.

According to this embodiment, as described above, the controller 31 is configured or programmed to linearly decrease the control parameter as the rotation speed ω increases. Accordingly, unlike a case in which the control parameter non-linearly changes, the control parameter for the rotation speed ω can be easily calculated.

According to this embodiment, as described above, the controller 31 is configured or programmed to decrease the control parameter as the rotation speed ω increases when the rotation speed ω is equal to or higher than the first rotation speed ω1 and equal to or lower than the second rotation speed ω2 that is higher than the first rotation speed ω1, and set the control parameter to a constant control parameter corresponding to the second rotation speed ω2 when the rotation speed ω exceeds the second rotation speed ω2. Accordingly, even when the rotation speed ω exceeds the second rotation speed ω2, an excessive decrease in the control parameter is significantly reduced or prevented, and thus the possibility that the user who operates the medical manipulator 1 feels uncomfortable with an operation (a difference between the amount of rotation of the pair of forceps 4b desired by the user and the actual amount of rotation) can be significantly reduced or prevented.

According to this embodiment, as described above, the controller 31 is configured or programmed to maintain the control parameter constant without decreasing it when the rotation speed ω is lower than the first rotation speed ω1. When the rotation speed ω of the shaft 4c is lower than the first rotation speed ω1, the rotation speed ω is relatively low, and thus vibrations of the manipulator arm 60 are relatively small. Therefore, when the rotation speed ω is lower than the first rotation speed ω1 as described above, the controller 31 maintains the control parameter constant without decreasing it such that the control load of the controller 31 can be decreased while vibrations of the manipulator arm 60 are significantly reduced or prevented.

According to this embodiment, as described above, the controller 31 is configured or programmed to generate the command value of the rotation speed ω according to the rotation speed ω with respect to the received amount of operation, apply the low-pass filter F to the generated command value, and decrease the control parameter to control the operation of the surgical instrument 4 when the command value is equal to or greater than the first rotation speed ω1 after the low-pass filter F is applied to the generated command value. Accordingly, the noise included in the command value of the rotation speed ω can be removed by the low-pass filter F.

According to this embodiment, as described above, the controller 31 is configured or programmed to decrease the control parameter to control the operation of the surgical instrument 4 when the rotation speed ω is equal to or higher than the first rotation speed ω1 while the surgical instrument 4 is bent such that the first support rotates about the J10 axis and intersects with the direction in which the shaft 4c extends. When the shaft 4c is rotated at a relatively high speed while the surgical instrument 4 is bent, vibrations of the manipulator arm 60 appear particularly remarkably. Therefore, as described above, decreasing the control parameter when the rotation speed ω is equal to or higher than the first rotation speed ω1 while the surgical instrument 4 is bent so as to intersect with the direction in which the shaft 4c extends is particularly effective in significantly reducing or preventing the vibrations of the manipulator arm 60.

Advantages of Control Method of Surgical System

According to this embodiment, as described above, the control method of the surgical system 100 includes changing the length L (control parameter) between the J10 axis and the J11 axis in the direction in which the shaft 4c extends according to the rotation speed ω of the shaft 4c with respect to the amount of operation according to the received operation to control the operation of the surgical instrument 4. Accordingly, even when the shaft 4c of the surgical instrument 4 is rotated at high speed, vibrations of the manipulator arm 60 can be significantly reduced or prevented.

MODIFIED EXAMPLES

The embodiment disclosed this time must be considered as illustrative in all points and not restrictive. The scope of the present disclosure is not shown by the above description of the embodiment but by the scope of claims for patent, and all modifications (modified examples) within the meaning and scope equivalent to the scope of claims for patent are further included.

For example, while the controller 31 is provided in the medical manipulator 1 in the aforementioned embodiment, the present disclosure is not limited to this. For example, the controller 31 may alternatively be provided in the remote operation device 2. Alternatively, the controller 31 may be provided separately from the medical manipulator 1 and the remote operation device 2, for example.

While the controller 31 linearly decreases the length L between the J10 axis and the J11 axis as the rotation speed ω of the shaft 4c increases in the aforementioned embodiment, the present disclosure is not limited to this. For example, the controller 31 may alternatively decrease the length L exponentially.

While the controller 31 maintains the length L, which is the control parameter, constant when the rotation speed ω of the shaft 4c exceeds the second rotation speed ω2 in the aforementioned embodiment, the present disclosure is not limited to this. For example, the controller 31 may alternatively gradually decrease the length L even when the rotation speed ω of the shaft 4c exceeds the second rotation speed ω2.

While the controller 31 does not decrease the length L, which is the control parameter, when the rotation speed ω of the shaft 4c is lower than the first rotation speed ω1 in the aforementioned embodiment, the present disclosure is not limited to this. For example, the controller 31 may decrease the length L according to the rotation speed ω whenever the shaft 4c rotates.

While the low-pass filter F is applied to the command value of the rotation speed ω in the aforementioned embodiment, the present disclosure is not limited to this. For example, the low-pass filter F may not be provided when the noise included in the command value of the rotation speed ω is small.

While the controller 31 decreases the length L (control parameter) regardless of whether or not the first support 4e intersects with the shaft 4c (the surgical instrument 4 is bent) in the aforementioned embodiment, the present disclosure is not limited to this. For example, the controller 31 may alternatively decrease the length L between the J10 axis and the J11 axis to control movement of the surgical instrument 4 when the rotation speed ω of the shaft 4c is equal to or higher than the first rotation speed ω1 while the surgical instrument 4 is bent such that the first support 4e rotates about the J10 axis and intersects with the direction in which the shaft 4c extends (only when the surgical instrument 4 is bent). Thus, when the surgical instrument 4 is not bent, a control to decrease the length L is not performed such that the control load of the controller 31 can be decreased.

While the four manipulator arms 60 are provided in the aforementioned embodiment, the present disclosure is not limited to this. In the present disclosure, the number of manipulator arms 60 may alternatively be any number as long as at least one manipulator arm 60 is provided.

While each of the arm portion 61 and the positioner 40 includes a 7-axis articulated robot in the aforementioned embodiment, the present disclosure is not limited to this. For example, each of the arm portion 61 and the positioner 40 may alternatively include an articulated robot having an axis configuration (six axes or eight axes, for example) other than the 7-axis articulated robot.

While the medical manipulator 1 includes the medical cart 3, the positioner 40, the arm base 50, and the manipulator arms 60 in the aforementioned embodiment, the present disclosure is not limited to this. For example, the medical manipulator 1 may not include the medical cart 3, the positioner 40, or the arm base 50, but may include only the manipulator arms 60.

The functionality of the elements disclosed herein may be implemented using circuitry or processing circuitry that includes general purpose processors, special purpose processors, integrated circuits, application specific integrated circuits (ASICs), conventional circuitry and/or combinations thereof that are configured or programmed to perform the disclosed functionality. Processors are considered processing circuitry or circuitry as they include transistors and other circuitry therein. In the present disclosure, the circuitry, units, or means are hardware that carries out or is programmed to perform the recited functionality. The hardware may be hardware disclosed herein or other known hardware that is programmed or configured to carry out the recited functionality. When the hardware is a processor that may be considered a type of circuitry, the circuitry, means, or units are a combination of hardware and software, and the software is used to configure the hardware and/or processor.

What is claimed is:

1. A robotic surgical system comprising:
a patient-side apparatus including a manipulator arm to which a surgical instrument is attached to a tip end side of the manipulator arm;
an operator-side apparatus including an operation unit to receive an operation on the surgical instrument; and
a controller configured or programmed to control operation of the surgical instrument based on an amount of operation corresponding to the operation; wherein
the surgical instrument includes:
an end effector;
a first support;
a second support; and
a shaft connected to the second support;
the first support supports the end effector such that the end effector is rotatable about a first axis that is orthogonal to a direction in which the shaft extends;
the second support supports the first support such that the first support is rotatable about a second axis that is spaced apart from the first axis in the direction in which the shaft extends and is orthogonal to the direction in which the shaft extends and the first axis; and the controller is configured or programmed to change a length between the first axis and the second axis in the direction in which the shaft extends, the length serving as a control parameter, according to a rotation speed of the shaft with respect to the amount of operation to control the operation of the surgical instrument.

2. The robotic surgical system according to claim 1, wherein the controller is configured or programmed to gradually decrease the control parameter as the rotation speed increases.

3. The robotic surgical system according to claim 2, wherein the controller is configured or programmed to linearly decrease the control parameter as the rotation speed increases.

4. The robotic surgical system according to claim 1, wherein
the controller is configured or programmed to:
decrease the control parameter as the rotation speed increases when the rotation speed is equal to or higher than a first rotation speed and equal to or lower than a second rotation speed that is higher than the first rotation speed; and
set the control parameter to a constant control parameter corresponding to the second rotation speed when the rotation speed exceeds the second rotation speed.

5. The robotic surgical system according to claim 4, wherein the controller is configured or programmed to maintain the control parameter constant without decreasing the control parameter when the rotation speed is lower than the first rotation speed.

6. The robotic surgical system according to claim 4, wherein the controller is configured or programmed to decrease the control parameter to control the operation of the surgical instrument when the rotation speed is equal to or higher than the first rotation speed while the surgical instrument is bent such that the first support rotates about the second axis and intersects with the direction in which the shaft extends.

7. The robotic surgical system according to claim 4, wherein
the controller is configured or programmed to:
generate a command value of the rotation speed according to the rotation speed with respect to the amount of operation;
apply a low-pass filter to the command value; and
decrease the control parameter to control the operation of the surgical instrument when the command value to which the low-pass filter has been applied is equal to or greater than the first rotation speed.

8. A patient-side apparatus comprising:
a manipulator arm to which a surgical instrument is attached to a tip end side of the manipulator arm; and
a controller configured or programmed to control operation of the surgical instrument based on an amount of operation corresponding to an operation on the surgical instrument received by an operation unit; wherein
the surgical instrument includes:
an end effector;
a first support;
a second support; and
a shaft connected to the second support;
the first support supports the end effector such that the end effector is rotatable about a first axis that is orthogonal to a direction in which the shaft extends;
the second support supports the first support such that the first support is rotatable about a second axis that is spaced apart from the first axis in the direction in which the shaft extends and is orthogonal to the direction in which the shaft extends and the first axis; and
the controller is configured or programmed to change a length between the first axis and the second axis in the direction in which the shaft extends, the length serving as a control parameter, according to a rotation speed of the shaft with respect to the amount of operation to control the operation of the surgical instrument.

9. The patient-side apparatus according to claim 8, wherein the controller is configured or programmed to gradually decrease the control parameter as the rotation speed increases.

10. The patient-side apparatus according to claim 9, wherein the controller is configured or programmed to linearly decrease the control parameter as the rotation speed increases.

11. The patient-side apparatus according to claim 8, wherein
the controller is configured or programmed to:
decrease the control parameter as the rotation speed increases when the rotation speed is equal to or higher than a first rotation speed and equal to or lower than a second rotation speed that is higher than the first rotation speed; and
set the control parameter to a constant control parameter corresponding to the second rotation speed when the rotation speed exceeds the second rotation speed.

12. The patient-side apparatus according to claim 11, wherein the controller is configured or programmed to maintain the control parameter constant without decreasing the control parameter when the rotation speed is lower than the first rotation speed.

13. The patient-side apparatus according to claim 11, wherein the controller is configured or programmed to decrease the control parameter to control the operation of the surgical instrument when the rotation speed is equal to or higher than the first rotation speed while the surgical instrument is bent such that the first support rotates about the second axis and intersects with the direction in which the shaft extends.

14. The patient-side apparatus according to claim 11, wherein
the controller is configured or programmed to:
generate a command value of the rotation speed according to the rotation speed with respect to the amount of operation;
apply a low-pass filter to the command value; and
decrease the control parameter to control the operation of the surgical instrument when the command value to which the low-pass filter has been applied is equal to or greater than the first rotation speed.

15. A control method executed by a controller of a robotic surgical system, the robotic surgical system including a patient-side apparatus including a manipulator arm to which a surgical instrument is attached to a tip end side of the manipulator arm, an operator-side apparatus including an operation unit to receive an operation on the surgical instrument, and the controller, the surgical instrument including an end effector, a first support, a second support, and a shaft connected to the second support, the first support supporting the end effector such that the end effector is rotatable about a first axis that is orthogonal to a direction in which the shaft extends, the second support supporting the first support such that the first support is rotatable about a second axis that is spaced apart from the first axis in the direction in which the shaft extends and is orthogonal to the direction in which the shaft extends and the first axis, the control method comprising:

receiving an amount of operation corresponding to the operation on the surgical instrument received by the operation unit; and changing a length between the first axis and the second axis in the direction in which the shaft extends, the length serving as a control parameter, according to a rotation speed of the shaft with respect to the amount of operation to control operation of the surgical instrument.

16. The control method according to claim 15, wherein the controller is configured or programmed to gradually decrease the control parameter as the rotation speed increases.

17. The control method according to claim 16, wherein the controller is configured or programmed to linearly decrease the control parameter as the rotation speed increases.

18. The control method according to claim 15, wherein the controller is configured or programmed to:

decrease the control parameter as the rotation speed increases when the rotation speed is equal to or higher than a first rotation speed and equal to or lower than a second rotation speed that is higher than the first rotation speed; and set the control parameter to a constant control parameter corresponding to the second rotation speed when the rotation speed exceeds the second rotation speed.

19. The control method according to claim 18, wherein the controller is configured or programmed to maintain the control parameter constant without decreasing the control parameter when the rotation speed is lower than the first rotation speed.

20. The control method according to claim 18, wherein the controller is configured or programmed to decrease the control parameter to control the operation of the surgical instrument when the rotation speed is equal to or higher than the first rotation speed while the surgical instrument is bent such that the first support rotates about the second axis and intersects with the direction in which the shaft extends.

* * * * *